United States Patent
Behlen et al.

(10) Patent No.: US 9,486,929 B2
(45) Date of Patent: Nov. 8, 2016

(54) SCREW CUTTING TOOL

(71) Applicant: Stryker Trauma SA, Selzach (CH)

(72) Inventors: Tobias Behlen, Aachen (DE); Manfred Schmuck, Muehlheim-Stetten/Donau (DE); Martin Knape, Freiburg (DE)

(73) Assignee: Stryker European Holdings I, LLC, Kalamazoo, MI (US)

( * ) Notice: Subject to any disclaimer, the term of this patent is extended or adjusted under 35 U.S.C. 154(b) by 254 days.

(21) Appl. No.: 14/041,311

(22) Filed: Sep. 30, 2013

(65) Prior Publication Data

US 2014/0090527 A1    Apr. 3, 2014

Related U.S. Application Data

(60) Provisional application No. 61/708,251, filed on Oct. 1, 2012.

(51) Int. Cl.
| | |
|---|---|
| *B26B 13/00* | (2006.01) |
| *B26B 13/22* | (2006.01) |
| *A61B 17/88* | (2006.01) |
| *B23D 29/02* | (2006.01) |
| *B23D 33/10* | (2006.01) |

(52) U.S. Cl.
CPC ........... *B26B 13/22* (2013.01); *A61B 17/8863* (2013.01); *B23D 29/023* (2013.01); *B23D 33/10* (2013.01); *B26B 13/00* (2013.01); *Y10T 83/04* (2015.04)

(58) Field of Classification Search
CPC ..... B25F 1/006; H02G 1/005; B23D 29/023; B23D 33/10; B26B 13/22; B26B 13/00; A61B 17/8863; B25B 7/22; Y10T 83/04
USPC ....... 30/90.1–91.2, 92, 22, 233, 287; 81/9.4, 81/9.44; 83/387
See application file for complete search history.

(56) References Cited

U.S. PATENT DOCUMENTS

| | | | |
|---|---|---|---|
| 2,494,996 A | | 1/1950 | Geddes |
| 2,543,018 A | | 2/1951 | Hainline |
| 2,997,787 A | * | 8/1961 | Wheeler ............. B23D 29/023 30/90.2 |
| 3,840,989 A | * | 10/1974 | Hexdall ............. B23D 29/023 30/231 |
| 4,215,598 A | | 8/1980 | Wells |
| 4,271,593 A | * | 6/1981 | Smith ................... H02G 1/005 30/233 |

(Continued)

FOREIGN PATENT DOCUMENTS

FR    955667 A    1/1950

OTHER PUBLICATIONS

Extended European Search Report for Application No. EP13186651.9 dated Feb. 14, 2014.

*Primary Examiner* — Ghassem Alie
*Assistant Examiner* — Nhat Chieu Do
(74) *Attorney, Agent, or Firm* — Lerner, David, Littenberg, Krumholz & Mentlik, LLP (57) ABSTRACT

A screw cutting tool for cutting a screw comprising a first grip having a first cutting aperture, a second grip pivotally connected to the first grip, the second grip having a second cutting aperture, a measuring scale attached to a proximal end of the first or second grip, and a screw holder slidably attached to the measuring scale having a hole extending therethrough, wherein the hole aligns with the first and second cutting apertures in at least one position.

10 Claims, 6 Drawing Sheets

(56) References Cited

U.S. PATENT DOCUMENTS 4,969,703 A * 11/1990 Fyfe .................... G02B 6/3636
                                                        30/90.1
5,201,254 A * 4/1993 Davies ................. H02G 1/1212
                                                        30/124
8,127,454 B1 * 3/2012 Gao .................... A61B 17/8863
                                                        30/92

* cited by examiner

SCREW CUTTING TOOL

CROSS-REFERENCE TO RELATED APPLICATIONS

The present application claims the benefit of the filing date of U.S. Provisional Patent Application No. 61/708,251 filed Oct. 1, 2012, the disclosure of which is hereby incorporated herein by reference.

BACKGROUND OF THE INVENTION

The present invention relates to a method and device used for the cutting of screws, specifically, a method and tool for accurately cutting the lengths of orthopedic screws.

Currently, a significant number of surgical implant systems that utilize screws are available. These systems typically include a number of different screw sizes, in both diameter and length, in order to accommodate the countless variables inherent in medical procedures. The inclusion of these varying screws, many of which end up unused, increases inventory and investment costs, as well as producing unnecessary waste. For instance, in the case of fracture fixation, systems include many differently sized bone plates and bone screws are provided, but only one plate and a few screws may be employed in a given procedure.

Additionally, even with the plethora of screws provided in a given system, the screws may not be provided in the necessary increments. For instance, the screw lengths may be incremented in multiples of five millimeters, but a given procedure may require an in-between size (e.g., a length in the two and a half increment range). This is particularly prevalent in surgeries that require a high degree of accuracy, such as cranio-maxillofacial surgery.

Thus, there exists a need for a method and apparatus for cutting screws to required lengths.

BRIEF SUMMARY OF THE INVENTION

One aspect of the present invention is a cutting tool with an attached measuring scale and screw holder allowing for a secure and accurate crop of a screw. Preferably, the cutting tool can be utilized in cutting screws having a variety of differing screw diameters. Additionally, the cutting tool catches the trimmed endpiece of the screw in order to facilitate easy and safe disposal of the endpiece.

In accordance with one embodiment, the tool is designed to cut a screw and includes first and second grips pivotally connected to each other, each having a cutting aperture, a measuring scale attached to a proximal end of the first grip, and a screw holder slidably attached to the measuring scale, having a hole extending therethrough, wherein the hole aligns with the first and second cutting apertures in at least one position.

In accordance with alternate embodiments, the tool may further include: a spring positioned against the first and second grips, wherein the spring biases the grips in an open position; multiple cutting sleeves within the first and second cutting apertures; a bracket capable of clamping the screw through manipulation of the grips about the pivotal connection, wherein the bracket rides along a pin engaged with slots on the bracket and both grips; a pivotal attachment between the measuring scale and the first or second grip; and additional cutting apertures on the first and second grips, with additional cutting sleeves therein.

In accordance with another alternate embodiment, the tool may include: a first grip having a first cutting aperture; a second grip pivotally connected to the first grip, the second grip having a second cutting aperture; a measuring scale attached to a proximal end of the first or second grip; a screw holder slidably attached to the measuring scale having a hole extending therethrough and aligning with the first and second cutting apertures in at least one position; a spring positioned against the first and second grips capable of biasing the grips to an open position; a first cutting sleeve disposed within the first cutting aperture; a second cutting sleeve disposed within the second cutting aperture; an arcuate slot extending through the proximal end of the first grip; a bracket having a linear slot and a polymeric end portion capable of clamping the screw against its polymeric end portion through manipulation of the grips; and a pin fixedly attached to the first grip and extending through and engaged within the arcuate slot and the linear slot.

Another aspect of the present invention is a method of cutting a screw utilizing a screw cutting tool.

In accordance with one embodiment, the screw is inserted through a hole in the screw holder and its corresponding first and second cutting apertures, the screw holder is slid along the measuring scale to determine the desired length to be cut, and the grips are actuated to cut the screw.

In accordance with alternate embodiments, the method may further include the steps of: clamping a trimmed endpiece of the screw for subsequent disposal, removing the holder from the measuring scale, and folding the measuring scale about a pivotal connection with the first or second grip.

DETAILED DESCRIPTION

Figure 1:
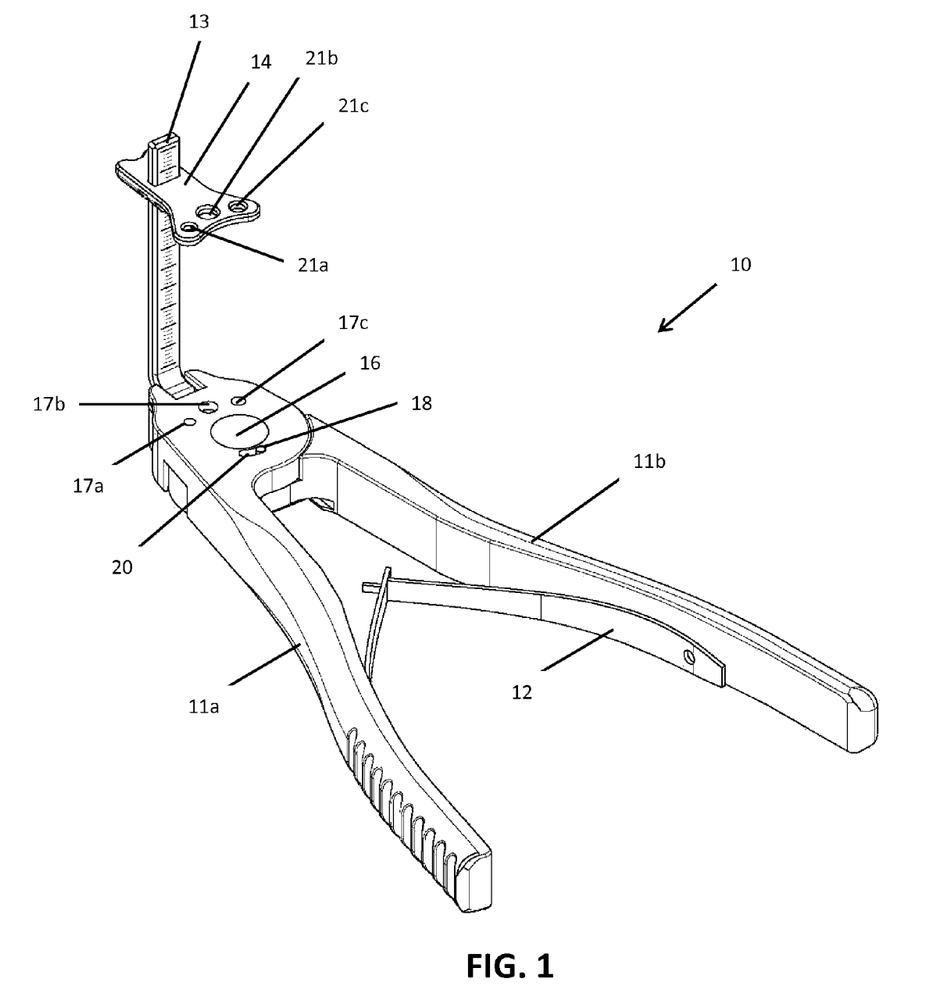
FIG. 1 is a perspective view of one embodiment of a screw cutting tool.

FIG. 1 shows a side view of one embodiment of screw cutting tool 10. Screw cutting tool 10 includes first grip 11a and second grip 11b, which are connected at a pivot 16. Each grip 11a, 11b features a spring 12 that is positioned between the grips 11a, 11b to bias them in the open position. A measuring scale 13 features one or more scales drawn or etched thereon for precisely measuring screw length and is pivotally attached at the proximal end of the first grip 11a, with a screw holder 14 slidably attached to the measuring scale 13. The pivotal connection of measuring scale 13 to the first grip 11a allows for the scale to be rotated into a folded configuration for easier storage of the tool. Likewise, the slidable connection of screw holder 14 with measuring scale 13 allows for the easy manipulation of that element, as well as for its removal to ease storage of the tool. It is to be understood that the measuring scale 13 could alternatively be attached to the proximal end of the second grip 11b.

Disposed on the first grip 11a, adjacent to pivot 16, are three apertures 17a, 17b, 17c of varying diameters to receive different diameters of screws. Likewise, screw holder 14 includes varying diameter apertures 21a, 21b, 21c to align with, and correspond to, the diameters of the respective apertures 17a, 17b, 17c below. Thus, a screw can be matched to the closest diameter among one of the apertures 21a, 21b, 21c of screw holder 14 and placed therethrough and into a corresponding aperture 17a, 17b, 17c.

Figure 2:
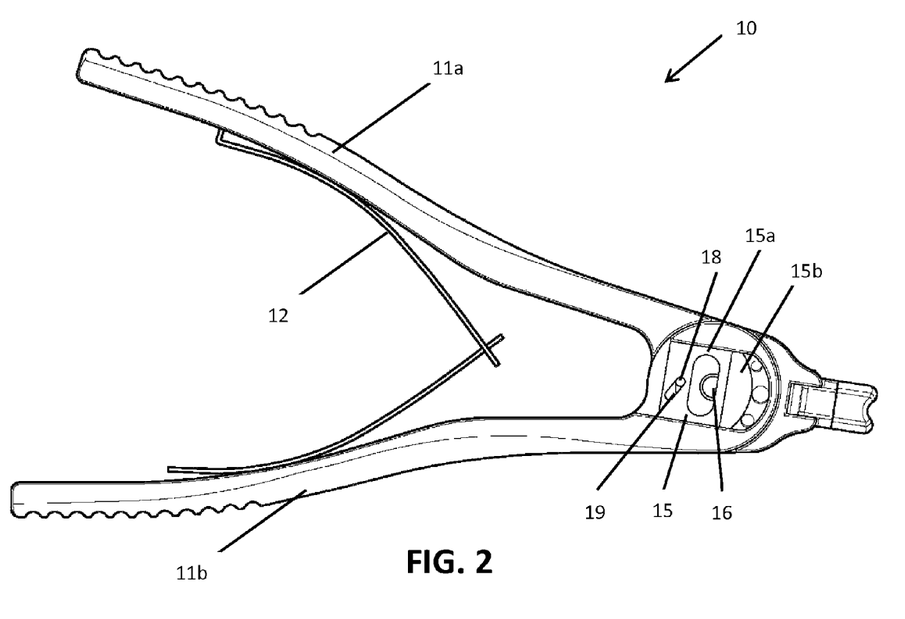
FIG. 2 is a bottom view of the embodiment of the screw cutting tool shown in FIG. 1.

As shown in FIG. 2, cutting tool 10 also includes a bracket 15 having a rigid slotted portion 15a and a polymeric end portion 15b attached below the pivot 16 for the purpose of trapping a trimmed endpiece of a screw against the end portion 15b after a cut is made (the cutting of the screw is discussed more fully below). A pin 18 is fixedly engaged with the first grip 11a (see FIG. 1) and is disposed within a linear slot 19 on the rigid slotted portion 15a of the bracket 15 and an arcuate slot 20 on the first grip 11a (see FIG. 1). As the grips 11 are squeezed together about the pivot 16, bracket 15 rides along the connection between the pin 18 and the linear slot 19 toward the resected screw, causing the polymeric end portion 15b to push against screw 2. The end portion 15b may thus hold the trimmed endpiece in place and prevent the endpiece from being lost.

Figure 3:
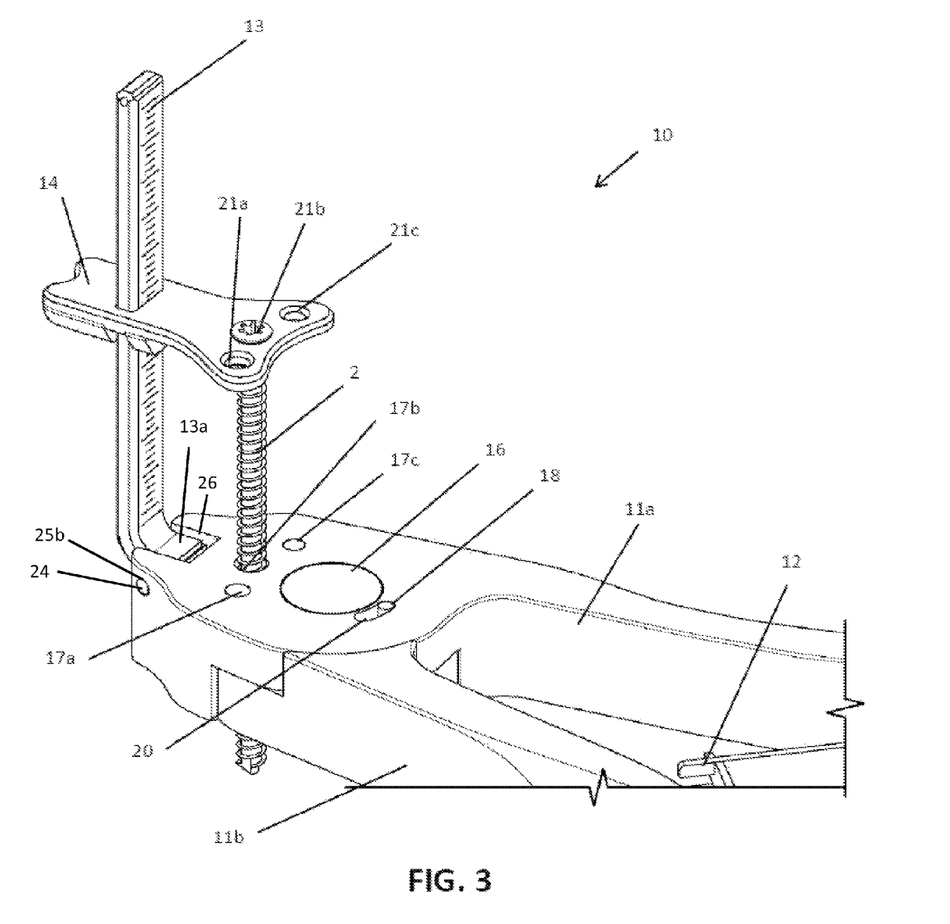
FIG. 3 is a perspective view of the embodiment of the screw cutting tool shown in FIG. 1, with a screw engaged with the cutting tool.
Figure 4A:
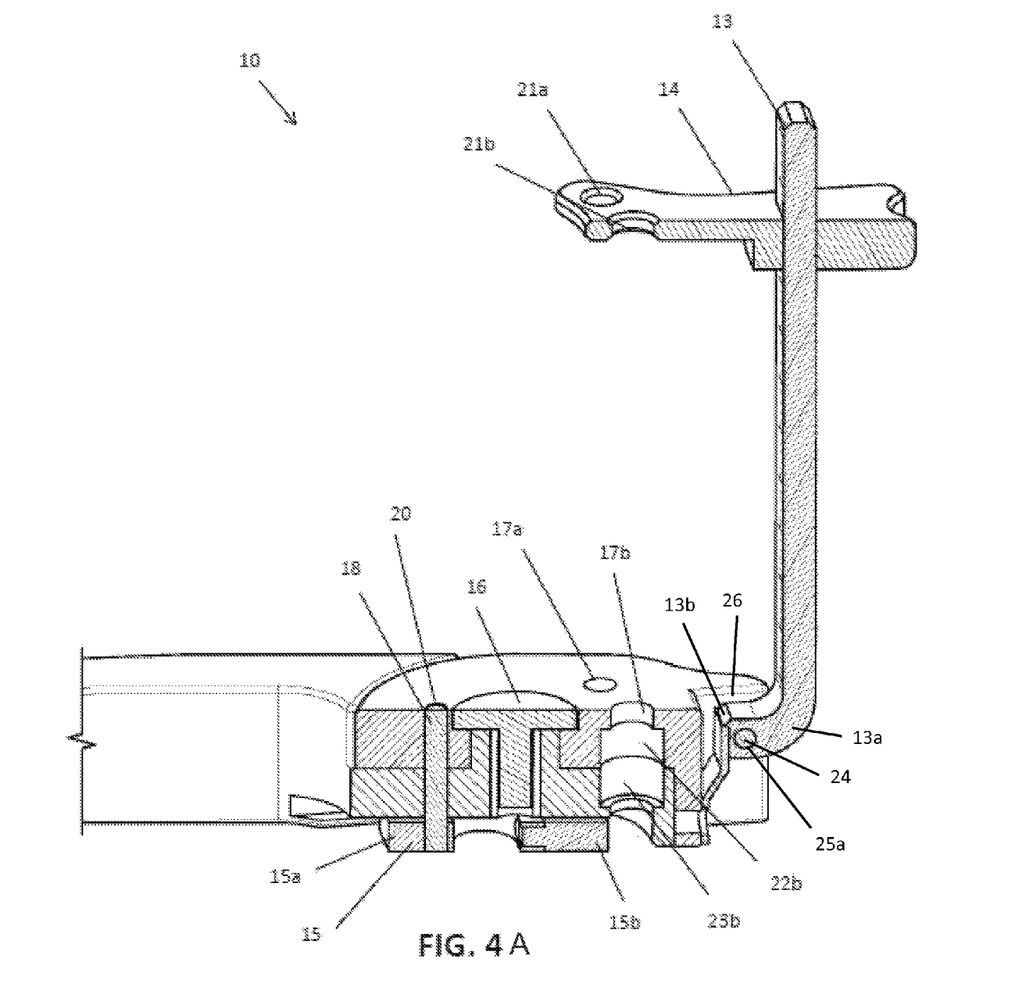
FIG. 4A is a cross-sectional side view of the embodiment of the screw cutting tool shown in FIG. 1, focused on the screw cutting portion of the tool.

FIG. 3 shows a perspective view of the cutting portion of the screw cutting tool 10. Screw 2 is inserted through aperture 21b and corresponding aperture 17b. By aligning the screw holder 14 with the desired length as indicated through the use of the measuring scale 13, screw 2 is held steady with the screw holder 14 in order to be cut to a desired length. Apertures 21a, 21b, 21c of holder 14 are sized so that a shank of screw 2 can pass therethrough, but its head cannot, such that screw 2 is essentially held in place by holder 14. The connection between the measuring scale 13 and the screw holder 14 may contain a locking mechanism (not shown) to keep the screw holder 14 locked against the desired increment of the scale 13 to ensure an accurate resection. A pivot end 13a of measuring scale 13 is pivotally attached to grip 11a by a pin 24 that inserted through a pin hole 25a (FIG. 4) in pivot end 13a and another pin hole 25b in grip 11a. As shown in FIG. 3, pivot end 13a is pivotable within an indention 26 of grip 11a.

Figure 4B:
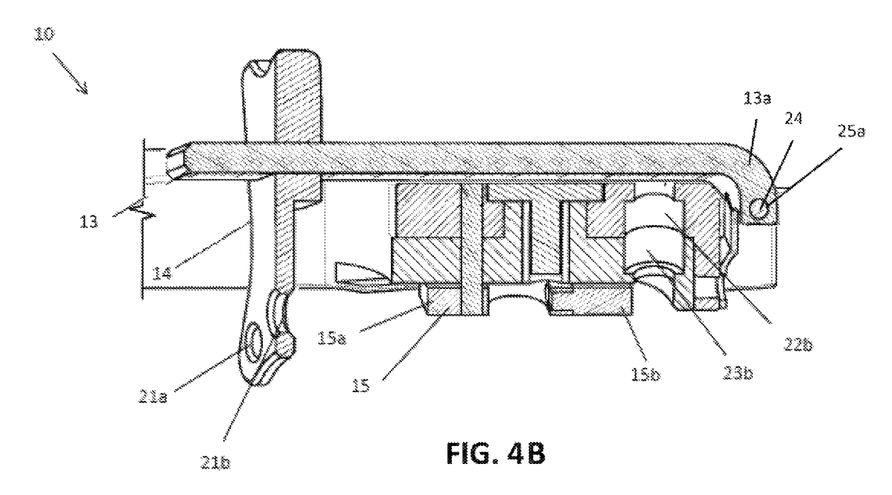
FIG. 4B is a cross-sectional side view of the embodiment of the screw cutting tool shown in FIG. 1, with the measuring scale pivoted with respect to the tool.
Figure 5:
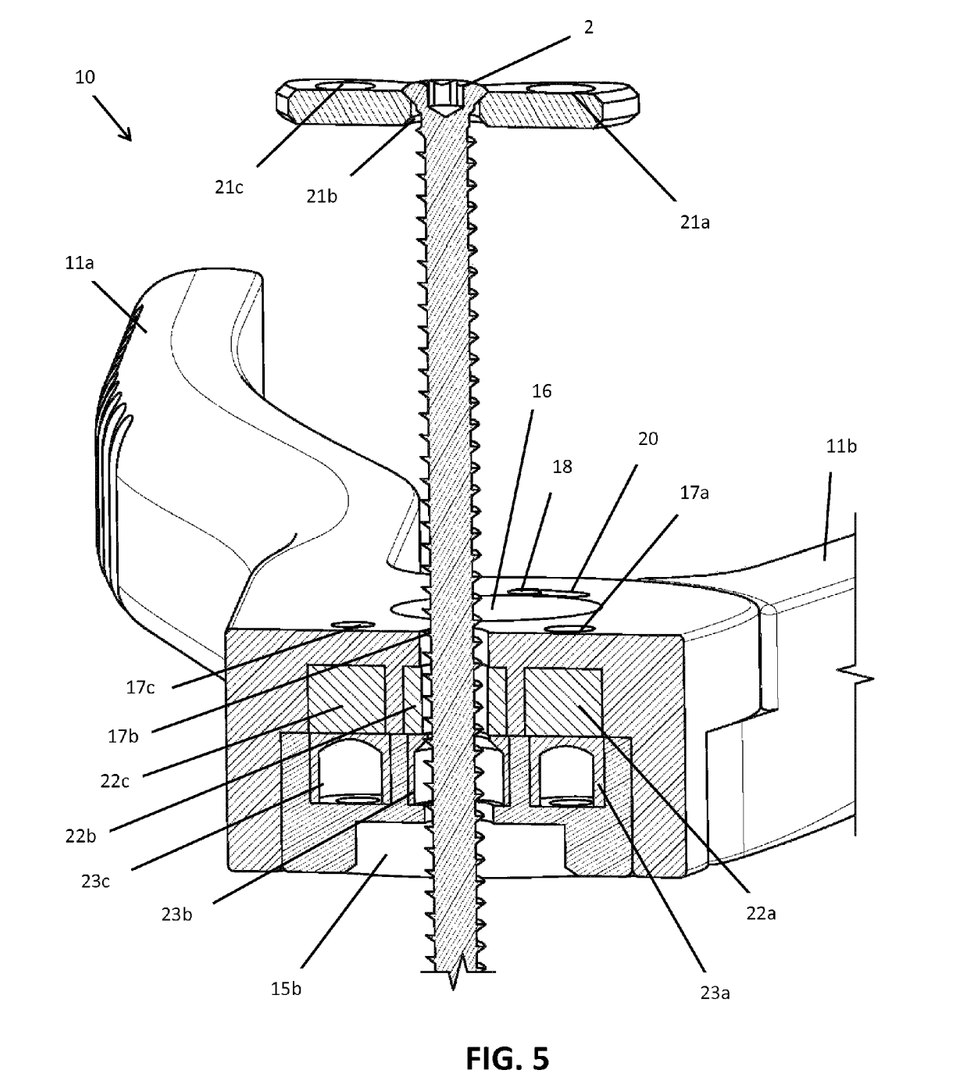
FIG. 5 is a cross-sectional front view of the embodiment of the screw cutting tool shown in FIG. 1, focused on the screw cutting portion of the tool.

FIGS. 4 and 5 respectively show cross-sectional side and front views of the screw cutting tool 10. First grip 11a features cutting sleeves 22a, 22b, 22c, while the second grip 11b features cutting sleeves 23a, 23b, 23c. The sleeves of both grips 11a, 11b are positioned such that they both align with their respective aperture 17a, 17b, 17c and contact each other (i.e., aperture 17a is aligned with sleeves 22a and 23a, and so forth). Cutting sleeves 22a, 22b, 22c and 23a, 23b, 23c are provided in different diameters to accommodate screws 2 of varying diameters. Moreover, the sleeves may be formed of a material hard enough to facilitate the cutting of screws 2 and may not necessarily be formed of the same material used for the rest of the tool 10. Suitable materials may be stainless steel, titanium or the like. Of course, the material may also be based upon the material of the given screws to be cut. The pivotal attachment between measuring scale 13 and grip 11a is also shown in FIG. 4, wherein pivot end 13a is depicted as having an exterior surface 13b that is, for example, chamfered for rotation against an interior surface of indention 26.

In one embodiment method according to the present invention, as shown in the figures, screw 2 is inserted through aperture 21b of screw holder 14 until a head thereof engages the holder 14. A portion of the shank of screw 2 necessarily extends into aperture 17b and thus the corresponding set of cutting sleeves 22b and 23b. Holder 14 may then be moved along scale 13 until the desired screw length is measured, whereupon the holder 14 may be held in place by a mechanism or other means to secure it against the measuring scale 13. First and second grips 11a, 11b may then be squeezed together, preferably under the power of a surgeon's hands. In this regard, first and second grips 11a, 11b may be of an ergonomic design, and may be designed to equate greater force to the shearing of screw 2 than is applied by the surgeon. In this regard, it is contemplated to incorporate a gearing system or the like into the tool 10. When first and second grips 11a, 11b are actuated about pivot 16, cutting sleeves 22b and 23b of their respective grips 11a, 11b move in opposing directions, thereby producing a shear force sufficient to shear screw 2 into two pieces. It is noted that as this shearing occurs, the portion sheared from the remainder of screw 2 is held in place by bracket 15. Thus, the operation of cutting tool 10 can be performed without worry of portions of screw 2 becoming dislodged therefrom and lost.

Although the embodiment depicted in FIGS. 1-5 is discussed in particular above, one skilled in the art would recognize that design variations are possible. For example, the number and shape of apertures 17a, 17b, 17c and corresponding cutting sleeves 22a, 22b, 22c and 23a, 23b, 23c provided could vary. Also, each of the cutting sleeves could be composed of a range of materials of sufficient hardness to cut screw 2 not limited by the range of materials used to make the rest of the tool 10 and the cutting sleeves may even be composed of different materials on a single tool 10. Likewise, the bracket 15 could be provided in a number of different shapes, with differently-shaped slots, or be composed of different materials sufficient to grip screw 2. Further still, spring 12 could be of any type that would bias the grips 11 apart.

Although the invention herein has been described with reference to particular embodiments, it is to be understood that these embodiments are merely illustrative of the principles and applications of the present invention. It is to be understood unless otherwise indicated herein that the figures are not intended to be to scale. It is therefore to be understood that numerous modifications may be made to the illustrative embodiments and that other arrangements may be devised without departing from the spirit and scope of the present invention as defined by the appended paragraphs.

The invention claimed is:

1. A screw cutting tool for cutting an end portion away from a screw and retaining the end portion, the tool comprising:
   a first grip having a first cutting aperture;
   a second grip pivotally connected to the first grip, the second grip having a second cutting aperture;
   a measuring scale attached to a proximal end of the first grip;
   an arcuate slot extending through the proximate end of the first grip;
   a screw holder slidably attached to the measuring scale having a hole extending therethrough;
   a bracket having a linear slot and a polymeric end portion, the bracket fixedly attached to the first grip and movable relative to the first grip in response to manipulation of the first and/or second grip about a pivotal connection so that in at least one position, the polymeric end portion holds the end portion of the screw in place; and
   a pin fixedly attached to the first grip and extending through and engaged within the arcuate slot and the linear slot, wherein the hole in the screw holder is aligned with the first and second cutting apertures in at least one position.

2. The screw cutting tool of claim 1, further comprising a spring positioned against the first and second grips, wherein the spring is capable of biasing the grips to an open position.

3. The screw cutting tool of claim 1, further comprising at least one cutting sleeve disposed within the first cutting aperture and at least one cutting sleeve disposed within the second cutting apertures.

4. The screw cutting tool of claim 1, wherein the measuring scale is pivotally attached to the proximal end of the first grip.

5. The screw cutting tool of claim 4, wherein the screw holder is removeable from the measuring scale.

6. The screw cutting tool of claim 1, wherein the first grip further comprises a third cutting aperture and the second grip further comprises a fourth cutting aperture.

7. The screw cutting tool of claim 6, further comprising at least one cutting sleeve disposed within the third cutting aperture and at least one cutting sleeve disposed within the fourth cutting apertures.

8. The screw cutting tool of claim 6, wherein the first grip further comprises a fifth cutting aperture and the second grip further comprises a sixth cutting aperture.

9. The screw cutting tool of claim 8, further comprising at least one cutting sleeve disposed within the fifth cutting aperture and at least one cutting sleeve disposed within the sixth cutting aperture.

10. A screw cutting tool for cutting a screw comprising:
a first grip having a first cutting aperture;
a second grip pivotally connected to the first grip, the second grip having a second cutting aperture;
a measuring scale attached to a proximal end of the first or second grip;
a screw holder slidably attached to the measuring scale having a hole extending therethrough and aligning with the first and second cutting apertures in at least one position;
a spring positioned against the first and second grips capable of biasing the grips to an open position;
a first cutting sleeve disposed within the first cutting aperture;
a second cutting sleeve disposed within the second cutting aperture;
an arcuate slot extending through the proximal end of the first grip;
a bracket having a linear slot and a polymeric end portion, the bracket being capable of clamping the screw against the polymeric end portion through manipulation of the grips; and
a pin fixedly attached to the first grip and extending through and engaged within the arcuate slot and the linear slot.

* * * * *